(12) United States Patent
VanderVeer

(10) Patent No.: US 8,454,975 B1
(45) Date of Patent: Jun. 4, 2013

(54) METHOD FOR ENHANCING SKIN APPEARANCE

(76) Inventor: Elizabeth VanderVeer, Lake Oswego, OR (US)

( * ) Notice: Subject to any disclaimer, the term of this patent is extended or adjusted under 35 U.S.C. 154(b) by 175 days.

(21) Appl. No.: 12/986,327

(22) Filed: Jan. 7, 2011

Related U.S. Application Data

(60) Provisional application No. 61/293,973, filed on Jan. 11, 2010.

(51) Int. Cl.
*A61K 38/16* (2006.01)

(52) U.S. Cl.
USPC ............. 424/239.1; 424/184.1; 424/234.1; 424/247.1; 514/17.7

(58) Field of Classification Search
None
See application file for complete search history.

(56) References Cited

U.S. PATENT DOCUMENTS

| | | | |
|---|---|---|---|
| 6,256,533 B1 | 7/2001 | Yuzhakov | |
| 6,558,361 B1 | 5/2003 | Yeshurun | |
| 6,821,281 B2 | 11/2004 | Sherman | |
| 7,591,806 B2 | 9/2009 | Xu | |
| 7,611,481 B2 | 11/2009 | Cleary | |
| 2004/0247623 A1* | 12/2004 | Cady | 424/239.1 |
| 2005/0036966 A1* | 2/2005 | Heckmann | 424/65 |
| 2005/0096632 A1 | 5/2005 | Pettis | |
| 2005/0261632 A1* | 11/2005 | Xu | 604/173 |
| 2007/0055192 A1* | 3/2007 | Alvarez | 602/29 |
| 2009/0012494 A1* | 1/2009 | Yeshurun et al. | 604/506 |
| 2009/0069741 A1* | 3/2009 | Altshuler et al. | 604/22 |
| 2009/0087457 A1* | 4/2009 | Dake et al. | 424/239.1 |
| 2009/0186052 A1* | 7/2009 | Cherif-Cheikh | 424/239.1 |
| 2009/0214685 A1* | 8/2009 | Hunt | 424/780 |
| 2010/0196445 A1* | 8/2010 | David et al. | 424/443 |
| 2010/0228225 A1* | 9/2010 | Cipolla | 604/506 |
| 2012/0039862 A1* | 2/2012 | Borodic | 424/94.64 |

FOREIGN PATENT DOCUMENTS

WO 00/74765 * 12/2000

* cited by examiner

*Primary Examiner* — Albert Navarro
*Assistant Examiner* — Ginny Portner
(74) *Attorney, Agent, or Firm* — Bert P. Krages, II

(57) ABSTRACT

A method for treating skin by administration of a neurotoxin such as a botulinum toxin by means of a dry needle. The method can be used to accomplish what has generally been described as skin rejuvenation and also to treat skin disorders such as skin lines, crepiness, excess skin, wrinkles, platysmal bands, uneven skin tone and color, and hyperhidrosis.

9 Claims, 5 Drawing Sheets

METHOD FOR ENHANCING SKIN APPEARANCE

CROSS-REFERENCED TO RELATED APPLICATIONS

This application claims the benefit of provisional application 61/293,973 which was filed on Jan. 11, 2010.

BACKGROUND OF THE INVENTION

The present invention relates to a method for treating skin by administration of a neurotoxin such as a botulinum toxin by means of a dry needle. The method can be used to accomplish what has generally been described as skin rejuvenation and also to treat skin disorders such as skin lines, crepiness, excess skin, wrinkles, platysmal bands, uneven skin tone and color, and hyperhidrosis.

SUMMARY OF THE INVENTION

The method makes use neurotoxins such as the type produced by the bacterium *Clostridium botulinum*. Among the serotypes of botulinum neurotoxins that can be used with the method are the serotypes A, B, Cl, D, E, F and G. These serotypes are produced by neutralization with type-specific antibodies and vary in their potency and the respective effects they exert among animal species. For example, botulinum neurotoxin type-A (BoNTA) can have an efficacy for up to 12 months. Other types of neurotoxins may be used with the method as well, including those made by other species of *Clostridium* such as *Clostridium tetani, Clostridium butyricum*, and *Clostridium beratti*. The Clostridial toxin used in the present method is preferably BoNTA.

The method consists of making small punctures into the epidermis and dermis encompassed by an area of treatment and then making a first application of a small amount of neurotoxin solution onto the outer surface of the skin. Additional punctures are then made followed by a second application of neurotoxin solution. The process of making the punctures reddens the skin (i.e., causes mild erythema) and may be generally perceived as irritating to the patient. In the preferred embodiment, the punctures are made using a hypodermic needle. However, other means of making punctures could be used such as using a solid needle, microknife, or microblade. In addition, the punctures can be made using devices on which multiple needles, blades, or acicular protuberances are mounted. The accumulation of punctures will manifest themselves in the form of skin appearance ranging from mild swelling and redness to pinpoint bleeding. Occasionally, a bruise may occur. The punctures allow the neurotoxin solution to permeate through the dermis and exert an effect on the underlying muscles to produce a beneficial treatment.

The amount of a neurotoxin selected for administration can be varied based upon criteria such as the severity and nature of the condition being treated, the characteristics of the neurotoxin toxin chosen, as well as the age, sex, body habitus, and health of the patient. For example, the effect of the treatment is generally proportional to the concentration of a neurotoxin in the solution administered. The method allows for precise control over the number, location, and spatial density of the punctures as well as control of the rate at which the punctures are made. The ability to control these factors is advantageous with respect to promoting efficacy of the procedure. Furthermore, the person administering the treatment can monitor the rate of absorption of the neurotoxin solution, evaluate the effect, maintain control of the procedure, and make adjustments accordingly. The two-application procedure has been found to be surprisingly advantageous with respect to the ability to monitor and control the application over single-application procedures. The method further allows the person administering the treatment to visually monitor for patient discomfort and to receive feedback from the patient. Methods for determining the appropriate dosage are generally determined on a case-by-case basis by the attending physician and are either routine to one of ordinary skill in the art or may be determined without an undue degree of experimentation. When the selected neurotoxin is BoNTA, the beneficial effects of the procedure generally last about three months.

DETAILED DESCRIPTION OF THE PREFERRED EMBODIMENT

Figure 1:
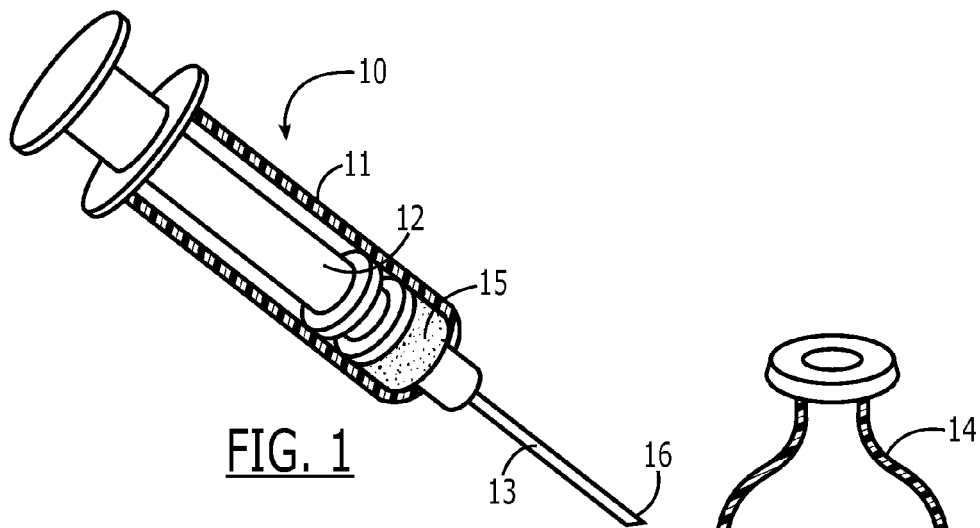
FIG. 1 is a schematic showing the syringe with hypodermic needle and container of neurotoxin.

FIG. 1 shows a syringe assembly 10 consisting of a syringe barrel 11, piston 12, and hypodermic needle 13. Also depicted is an injection vial 14 of neurotoxin which has been rendered into a solution 15 by injecting a fluid such as normal saline into the vial. Afterwards, the needle 13 is inserted into the injection vial 14 and the piston 12 is withdrawn so as to fill the barrel 11 with the desired amount of neurotoxin solution 15. It should be noted that the invention is not dependent on using a syringe 10 of the kind shown in the figures and that any method of applying a neurotoxin solution is acceptable such as swabs, pipettes, or pouring from glassware such as beakers. However, due to the typical packaging of neurotoxin in injection vials, the use of a hypodermic syringe and needle is preferred as this combination expedites the administration of the treatment. The type and volume of the syringe may encompass the kinds commonly used in the medical professions for hypodermic injections but it is preferred that the syringe be of a size that is easily held and controlled by the person administering the treatment and that the syringe have sufficient volume to hold all the neurotoxin solution required during the administration of the treatment. A needle ranging in gauge from 25 to 34 is preferred and ranging in gauge from 29 to 32 even more preferred.

Enough neurotoxin solution 15 should be prepared to carry the neurotoxin to the treatment area which it is covers. In addition, the solution should be made with sufficient neurotoxin to effect the treatment. The specific dilutions may vary depending on the particular neurotoxin formulation being administered.

Prior to the performance of the procedure, the patient is positioned in a chair in a semirecumbent position and the area of treatment exposed, for example, by removing clothing or jewelry in the vicinity of the area to be treated. Towels may be placed around the area of treatment to isolate the treatment area and prevent hair or fabric from contacting the treatment area during the procedure. The outer surface of the skin in the area of the treatment is cleaned and disinfected by wiping with an antiseptic or disinfectant such as alcohol and allowing the skin to dry.

Figure 2:
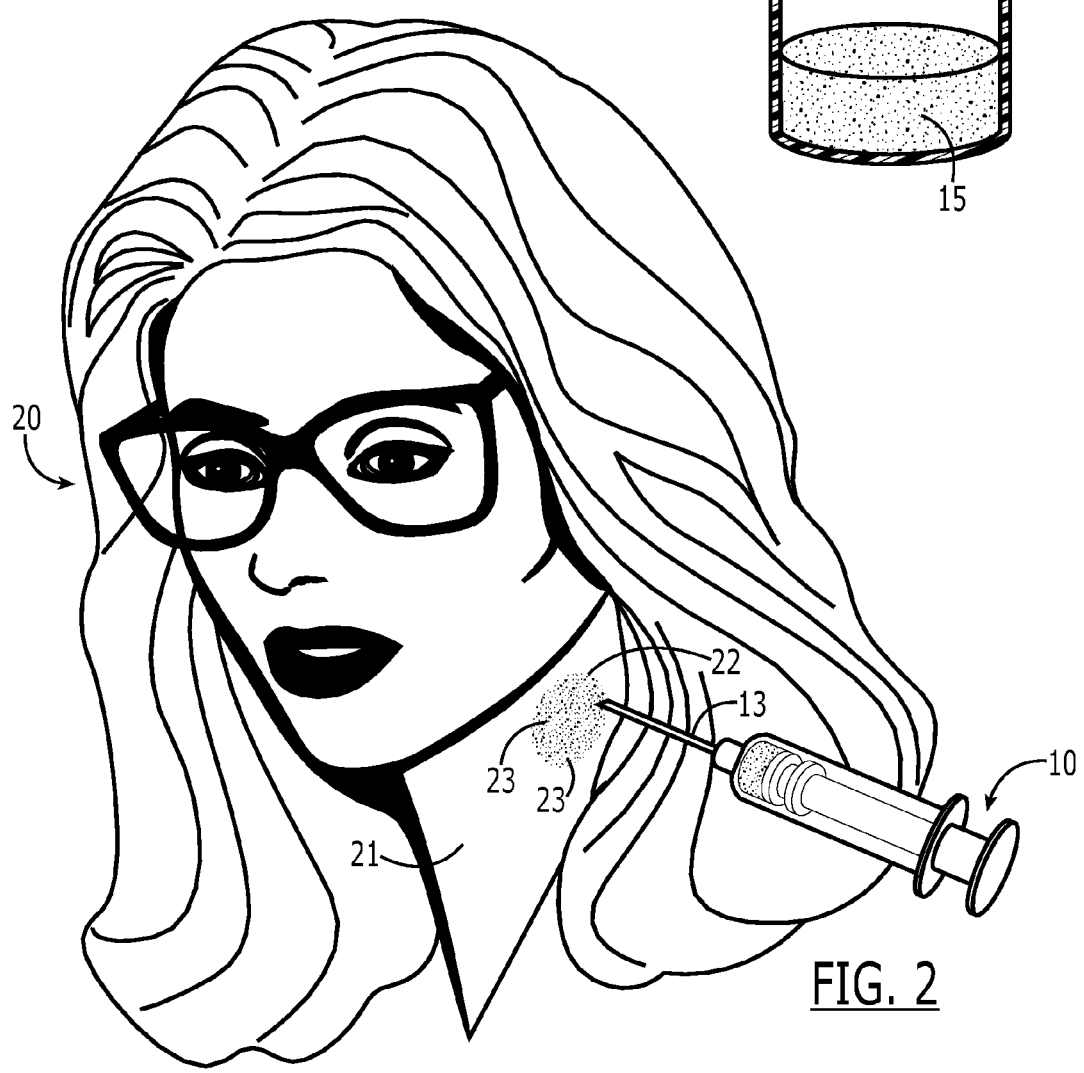
FIG. 2 is a view of a treatment area on the neck of a patient showing the puncture-making process.
Figure 3:
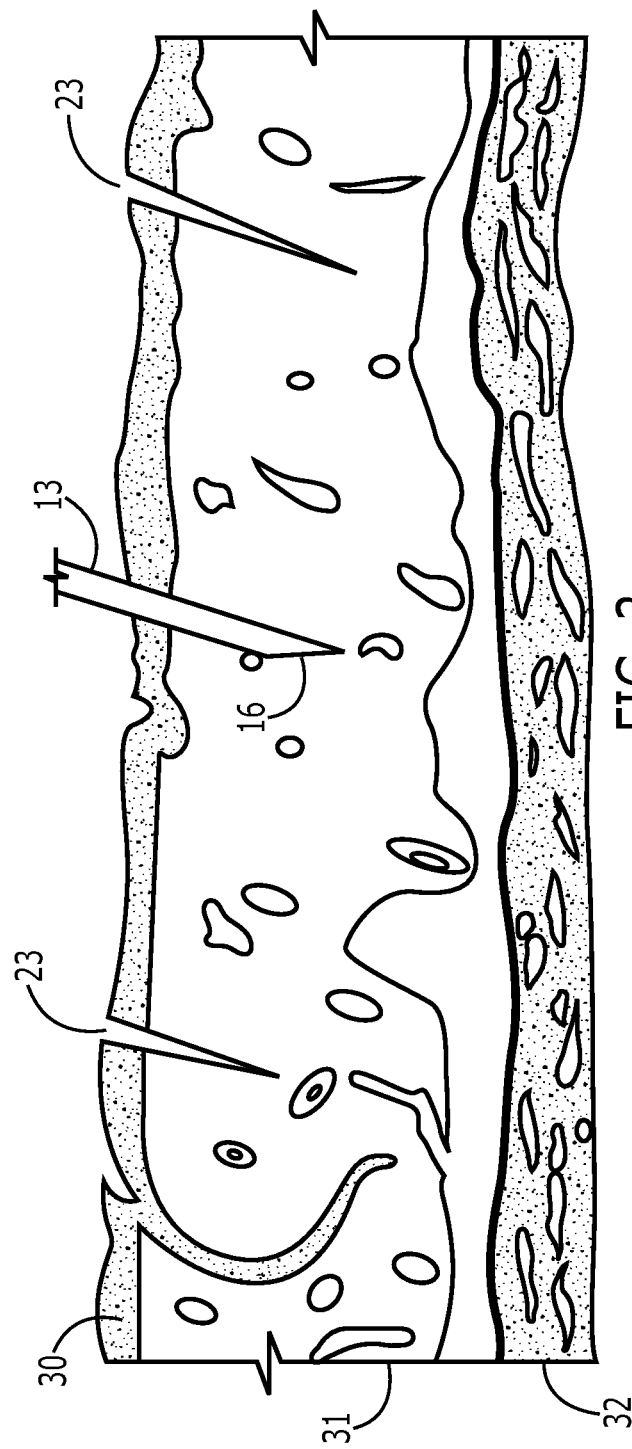
FIG. 3 is a side view showing the penetration of a hypodermic needle into the dermis.

FIG. 2 depicts the procedure being conducted on a treatment area 22 of the neck 21 of a patient 20. The hypodermic needle 13 is "bounced" across the treatment area 22 in a random but somewhat organized manner to produce serial punctures. As shown in FIG. 3, the point 16 of the needle 13 incises through the epidermis 30 into the dermis 31 but not into the hypodermis 32. Preferably, the punctures 23 are created by pushing downward with the face of the beveled portion of the point 16 oriented so that it is perpendicular to the surface of the skin. Generally, the syringe 11 will be held at a 45-degree angle to the skin and moved in a downward-and-upward motion perpendicular to the surface of the skin. The depth of the punctures 23 created by the needle 13 will vary depending on the thickness of the epidermis and dermis. The epidermis varies in thickness depending on the part of the body. Its thickness can be up to a millimeter or more in areas such as the palms and soles and may be only a tenth of a millimeter over the eyelids but is generally about a half-millimeter over most of the body. The dermis ranges one to four millimeters in thickness being about half a millimeter over the eyelids and several millimeters over portions of the back. In the more commonly areas receiving the treatment, such as the neck, the punctures 23 are made to a depth of less than 1 millimeter and generally less than 0.5 millimeters using a 31 gauge needle 13.

Figure 4:
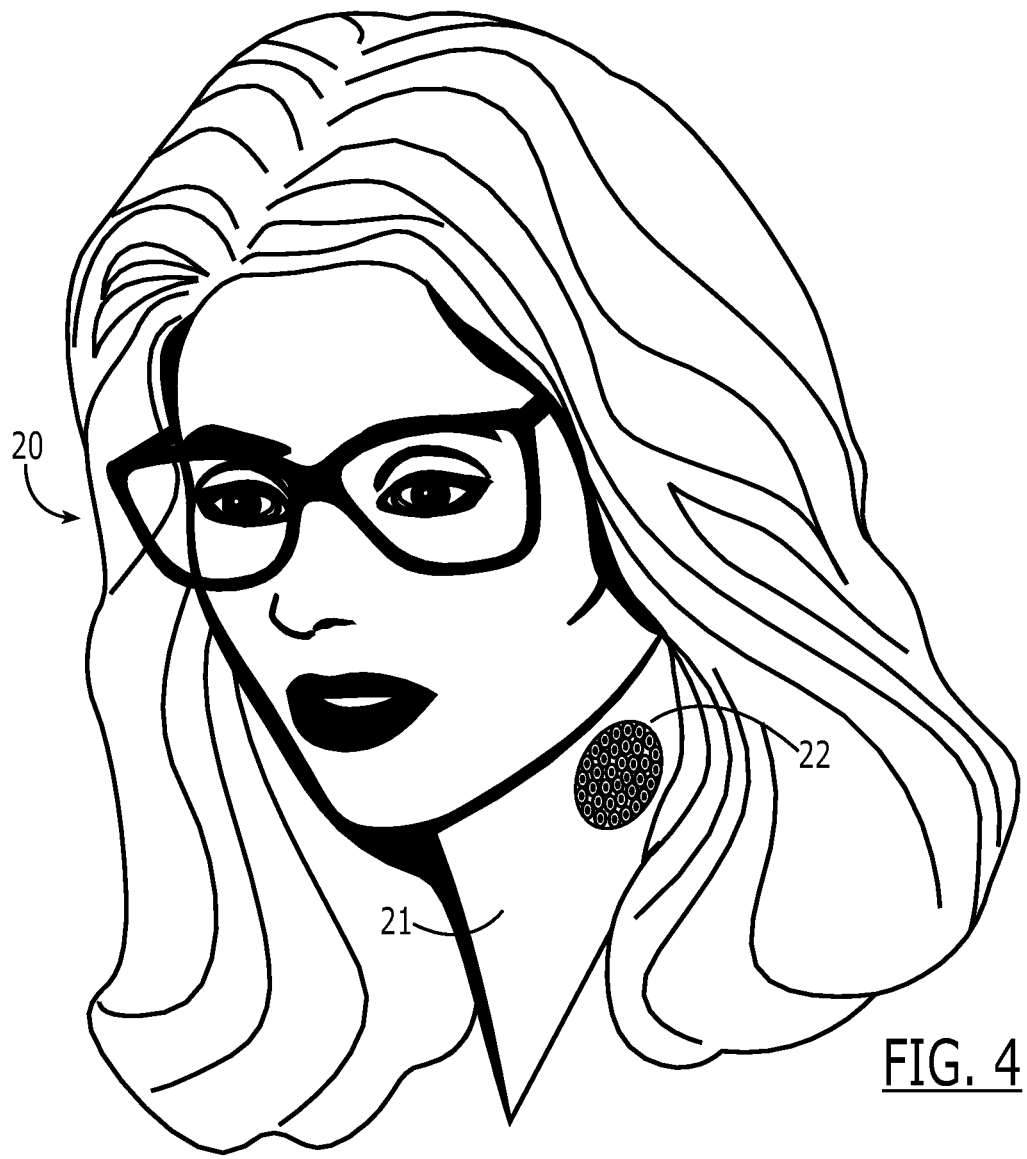
FIG. 4 is a view of a treatment area on the neck of a patient showing the erythema associated with the punctures.
Figure 5:
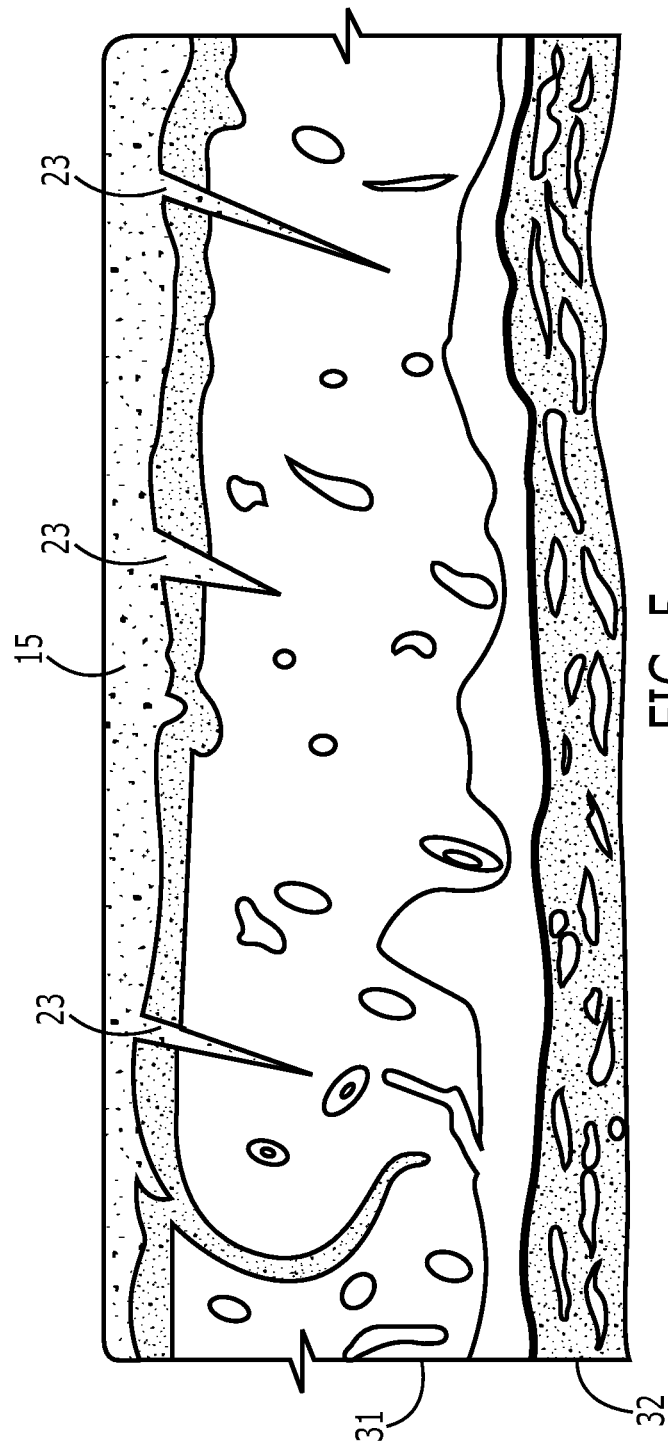
FIG. 5 is a side view showing several punctures into the dermis and the overlying film of neurotoxin solution.
Figure 6:
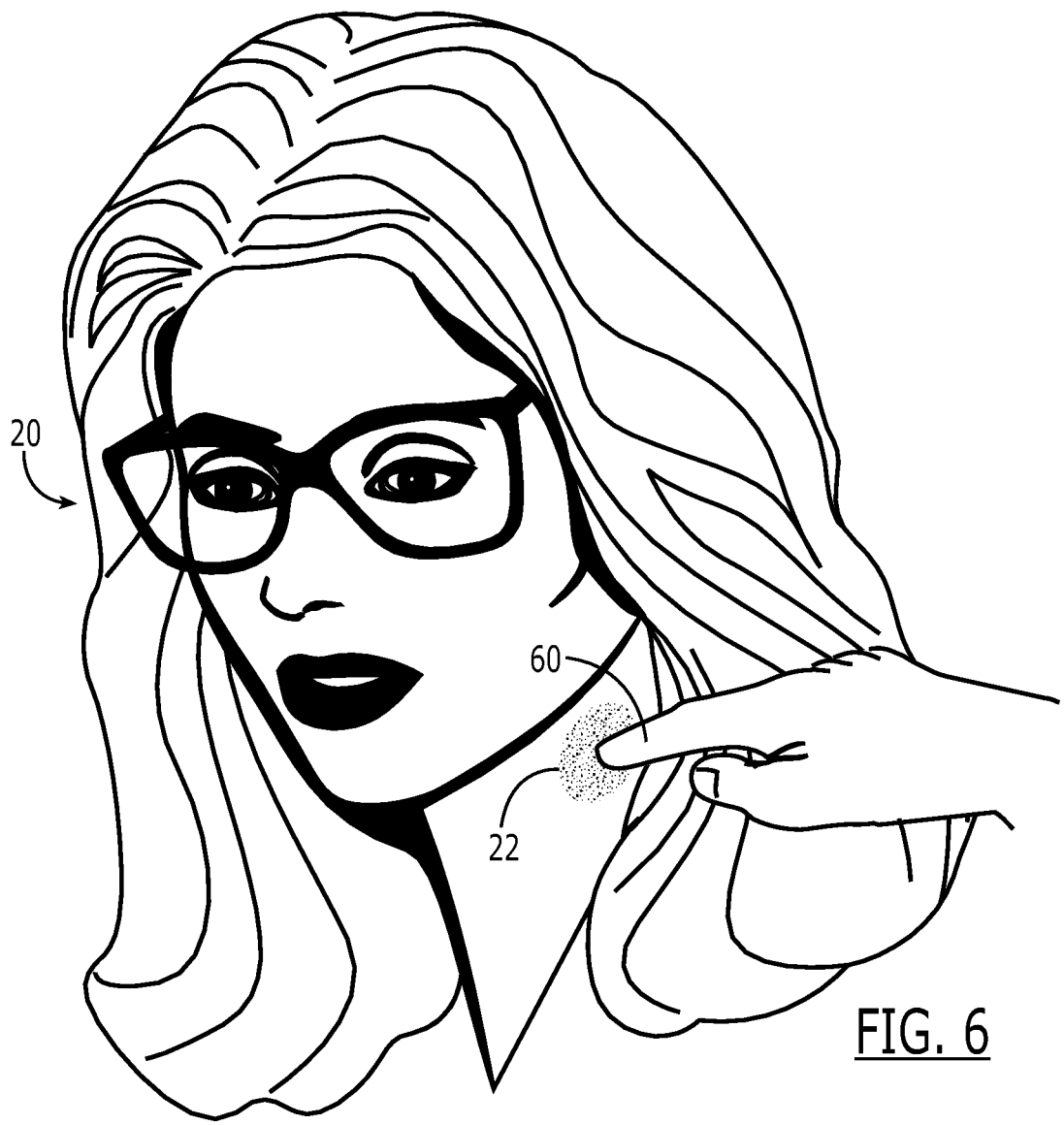
FIG. 6 is a view of a treatment area on the neck of a patient showing a gloved finger massaging the treatment area to promote absorption of the fluid.

The process of creating punctures is continued until mild erythema 24 is present over the treatment area 22 as shown in FIG. 4. In some cases, pinpoint bleeding may occur. At this point, the needle 13 is positioned close to but not touching the skin and the piston 12 of the hypodermic syringe 10 is very slowly depressed to apply small drops of the neurotoxin solution 15 over the area encompassed by the punctures 23 until the treatment area 22 is covered by a thin film of neurotoxin solution 15 as shown in FIG. 5. Additional punctures 23 are then made into the treatment area 22 with particular attention paid to the problem areas such as skin lines, crepiness, excess skin, platysmal bands, and uneven skin tone and color. Afterwards, more drops of neurotoxin solution 15 are applied in the manner just described. All the neurotoxin solution 15 is allowed to absorb into treatment and none is blotted. However, a gloved finger 60 may be used to rub the treatment area 22 to facilitate the absorption of the neurotoxin solution 15. By the end of the procedure, the treatment area will be covered by about five to ten punctures per square centimeter.

In the preferred embodiment, about 1 cubic centimeter of BoNTA solution will be applied to a treatment area on the neck having an area of about 100 square centimeters. The solution will typically take about 5 minutes to absorb into the skin after cessation of creating the punctures. It should be noted that the number of punctures per square centimeter to allow absorption of the neurotoxin solution will vary depending on the characteristics of the skin such as thickness and permeability and in some instances a lesser or greater number of punctures may be required than the five to ten typically associated with the treatment of the skin surface over the neck.

Following the procedure, the treatment area is kept clean and not wiped or washed for at least two hours. The patient is also instructed not to engage in any activity that might induce appreciable sweating at or near the treatment area such as physical activity and to avoid exposure to heat or sunlight.

EXAMPLE

Use of a Botulinum Toxin to Treat Rhytids, Skin Laxity, Texture, Tone, and Color Irregularities of the Neck A 50 year-old female patient with an "aging neck" exhibiting rhytids, skin laxity, texture, tone, and color irregularities was treated using the method. An area of about 100 square centimeters was treated by applying small punctures in accordance with the method previously described until the treatment area exhibited pinpoint bleeding, erythema, and edema. About 25 units of BOTOX (onabotulinumtoxin A marketed by Allergan, Inc.), diluted with normal saline was initially applied over the treatment area and gently rubbed until the solution was absorbed by the skin. A subsequent round of punctures were made to the treatment area followed by the application and absorption of the remainder of the BOTOX solution so that a total of 50 units was applied to and absorbed by the skin and hemostasis was achieved. The treatment was repeated two weeks later. Clinically-significant improvement was noted with respect to rhytids, skin laxity, texture, tone, and color irregularities. The patient reported very high satisfaction with the results and no difficulties in swallowing or decrease in neck strength was noted. Positive effects lasted for at least three months based on the observations by the treating physician and subjective reports by the patient.

As will be apparent to a person skilled in the art, a number of variations and modifications can be made to the structure described above without departing from the spirit and scope of the present invention.

I claim:

1. A method for treating skin by administration of a neurotoxin solution to a human subject, comprising the steps of:
   a. defining a treatment volume having an outer surface and encompassing epidermis, dermis, and hypodermis;
   b. making a first plurality of punctures inside the treatment volume that penetrate through the epidermis and terminate within the dermis, and without penetrating into the hypodermis;
   c. applying the neurotoxin solution to the outer surface of the treatment volume to create a film of said neurotoxin solution on the outer surface, in which the neurotoxin solution comprises BoNTA and which is applied at 0.01 cubic centimeters per square centimeter of outer surface;
   d. making a second plurality of punctures into the treatment area that penetrate through the epidermis and terminate within the dermis, and without penetrating into the hypodermis;
   e. adding an additional amount of said neurotoxin solution to the outer surface; and
   f. allowing the neurotoxin solution to absorb into said treatment volume and penetrate into the hypodermis; and
   g. ensuring that the outer surface of the treatment volume is exposed to air but not wiped for at least two hours following the absorption of said neurotoxin solution.

2. A method for treating skin by administration of a neurotoxin solution to a human subject, comprising the steps of:
   a. defining a treatment volume having an outer surface area and encompassing epidermis, dermis, and hypodermis;
   b. for every 100 square centimeters of said outer surface area, diluting 50 units of BoNTA with saline to form a neurotoxin solution volume;

c. making a first plurality of punctures inside the treatment volume that penetrate through the epidermis and terminate within the dermis, and without penetrating into the hypodermis;

d. applying half of the neurotoxin solution volume to the outer surface area of the treatment volume to create a film of said neurotoxin solution on the outer surface;

e. making a second plurality of punctures into the treatment area that penetrate through the epidermis and terminate within the dermis, and without penetrating into the hypodermis;

f. applying the remaining amount of said neurotoxin solution volume to the outer surface area to augment said film; and g. allowing the neurotoxin solution to absorb into said treatment volume and penetrate into the hypodermis.

3. The method of claim 2 in which the punctures are made using a needle.

4. The method of claim 2 in which the absorption of neurotoxin solution is aided by massaging the treatment area.

5. The method of claim 2 further comprising an additional step of instructing said human subject not to engage in activity that might induce sweating for at least two hours following absorption of said neurotoxin solution.

6. The method of claim 2 in which the number of punctures range between 5 to 10 per square centimeter of outer surface.

7. The method of claim 2 in which the steps are repeated 14 days later.

8. A method for treating skin by administration of a neurotoxin solution to a human subject, comprising the steps of:

a. defining a treatment volume having an outer surface and encompassing epidermis, dermis, and hypodermis;

b. making a first plurality of punctures inside the treatment volume that penetrate through the epidermis and terminate within the dermis, and without penetrating into the hypodermis;

c. applying the neurotoxin solution to the outer surface of the treatment volume to create a film of said neurotoxin solution on the outer surface;

d. making a second plurality of punctures into the treatment area that penetrate through the epidermis and terminate within the dermis, and without penetrating into the hypodermis, such that the number of punctures range between 5 to 10 per square centimeter of outer surface;

e. adding an additional amount of said neurotoxin solution to the outer surface to augment said film; and f. allowing the neurotoxin solution to absorb into said treatment volume and penetrate into the hypodermis.

9. The method of claim 8 further comprising the steps of:

g. ensuring that the outer surface of the treatment volume is exposed to air but not wiped for at least two hours following the absorption of said neurotoxin solution; and h. instructing said human subject not to engage in activity that might induce sweating for at least two hours following absorption of said neurotoxin solution.

* * * * *